United States Patent
Mauze et al.

(10) Patent No.: US 6,202,480 B1
(45) Date of Patent: Mar. 20, 2001

(54) THERMOMETRIC VAPOR SENSOR WITH EVAPORATION SURFACE HAVING MICROPORES

(75) Inventors: Ganapati R. Mauze, Sunnyvale; Michael Greenstein; Paul Lum, both of Los Altos; Hewlett E. Melton, Jr., Sunnyvale, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/054,852

(22) Filed: Apr. 2, 1998

(51) Int. Cl.$^7$ .............................. G01N 25/62; G01N 7/00; G01K 3/00
(52) U.S. Cl. ............................... 73/77; 73/64.45; 374/109
(58) Field of Search .................. 73/77, 64.45, 64.44, 73/335.06; 374/109, 28

(56) References Cited

U.S. PATENT DOCUMENTS

| | | | |
|---|---|---|---|
| 1,484,129 | 2/1924 | Hermann et al. | 73/335.08 |
| 1,586,351 | 5/1926 | Bristol et al. | 73/335.08 |
| 2,494,769 | 1/1950 | Mabey | 73/335.08 |
| 3,603,135 | 9/1971 | Kawaguchi | 73/29 |
| 5,048,336 | 9/1991 | Sugihara | 73/336.5 |
| 5,460,041 | 10/1995 | Andes et al. | 73/335.08 |
| 5,608,374 | 3/1997 | Ikejiri | 338/35 |

OTHER PUBLICATIONS

MiniCap 2—Relative Humidity Sensor.
R. H. Perry, et al., "Psychometry"; Chemical Engineering Handbook, 5th Ed., pp. 12–2 to 12–5.
S. Tsuchitani, T. Sugawara, N. Kinjo, and S. Ohara, "A Humidity Sensor Using Ionic Copolymer and Its Application to a Humiity–Temperature Sensor Module", Sensors and Actuators, 15 (1988) pp. 375–386.
A. D. Elsner and T. B. Martonen, "Design and Development of a Micro–Thermocouple Sensor for Determining Temperature and Relative Humidity Pattenrs Within an Airstream", Journal of Biomechanical Engineering, Nov., 1989, vol. 111, pp–283–287.
Jay W. Grate and Mark Klusty, "Surface Acoustic Wave Vapor Sensors Based on Resonator Devices", Anal. Chem., Nov., 1991, vol. 63, pp–1719–1727.
Hy–Cal Engineering, IC Humidity/Temperature Sensor.
Hy–Cal, Humidity Sensor Theory and Behavior.
W. L. McCabe, et al., "Humidification Operation", Unit Operation of Chemical Engineering, 2nd Edition, Mass Transfer and Its Applications, Chapter 22, pp. 678–706.

*Primary Examiner*—Hezron Williams
*Assistant Examiner*—Jay L. Politzer
(74) *Attorney, Agent, or Firm*—Michael J. Beck

(57) ABSTRACT

A sensor for sensing in a gas stream a vapor of a liquid. The sensor includes a micropore and a wet temperature sensor. The micropore has an evaporation end and has a lumen to conduct liquid from a supply of the liquid for evaporation at the evaporation end. The wet temperature sensor has a heat sensitive part in contact with the liquid in the micropore. The heat sensitive part circumscribes the micropore and forms part of the lumen. Heat loss due to evaporation of the liquid when the wet temperature sensor wet with the liquid is placed in the gas stream will result in the temperature sensed by the wet temperature sensor being lower than the non-evaporative temperature of the gas stream. This lowering in temperature can be measured to determine the concentration of the vapor in the gas stream. An example of such a sensor has a thermocouple junction having micropores passing through the thermocouple junction.

12 Claims, 14 Drawing Sheets

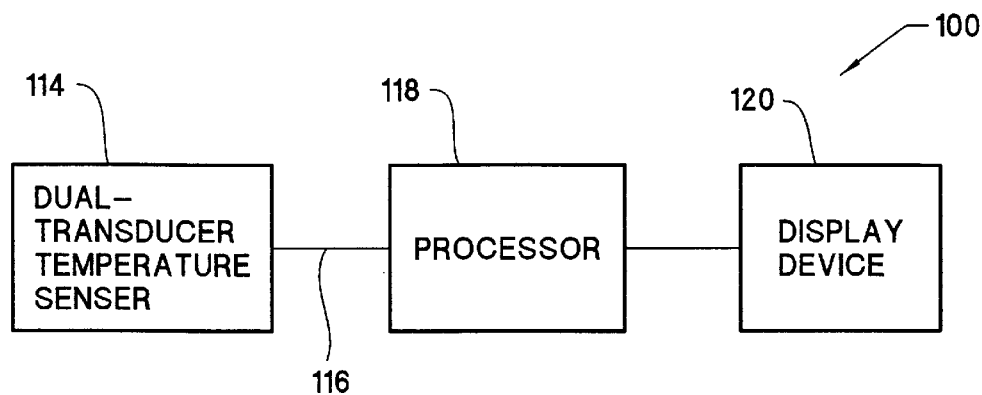
Fig. 1
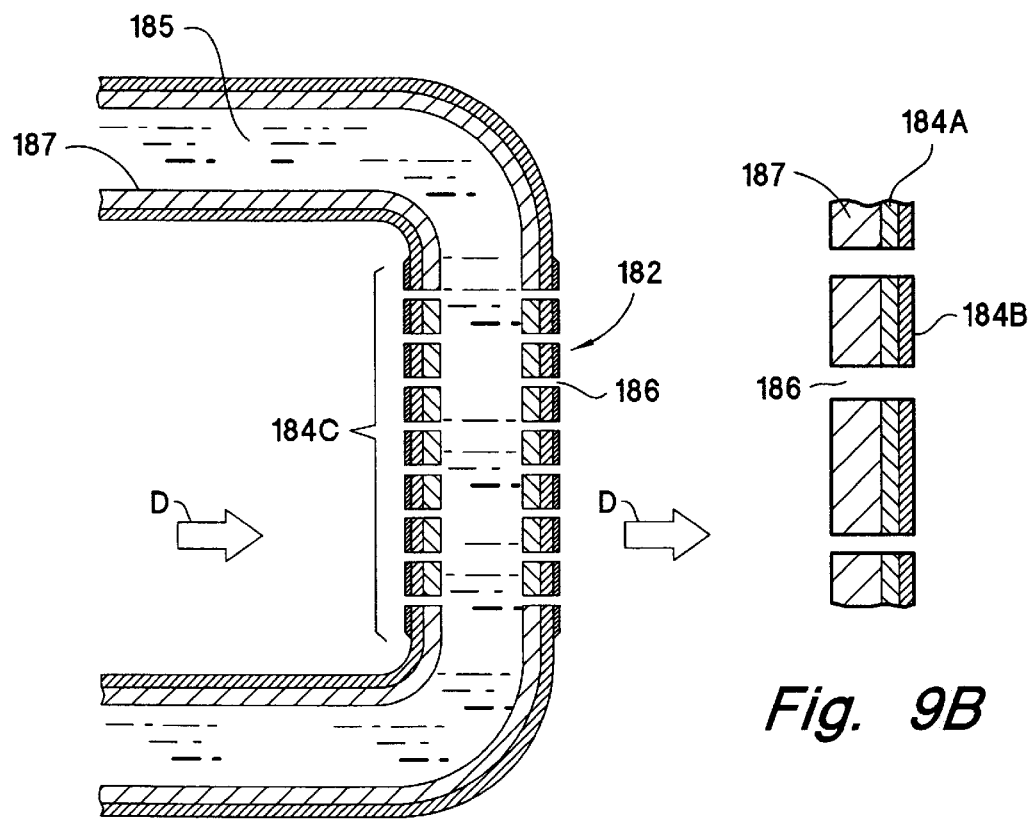
Fig. 9A
Fig. 9B

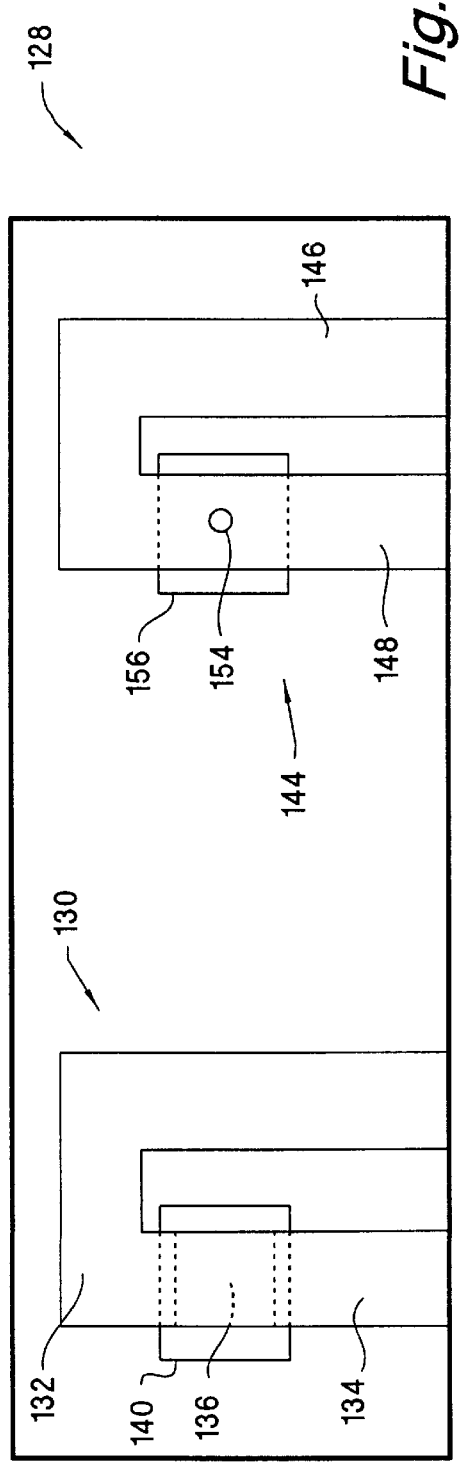
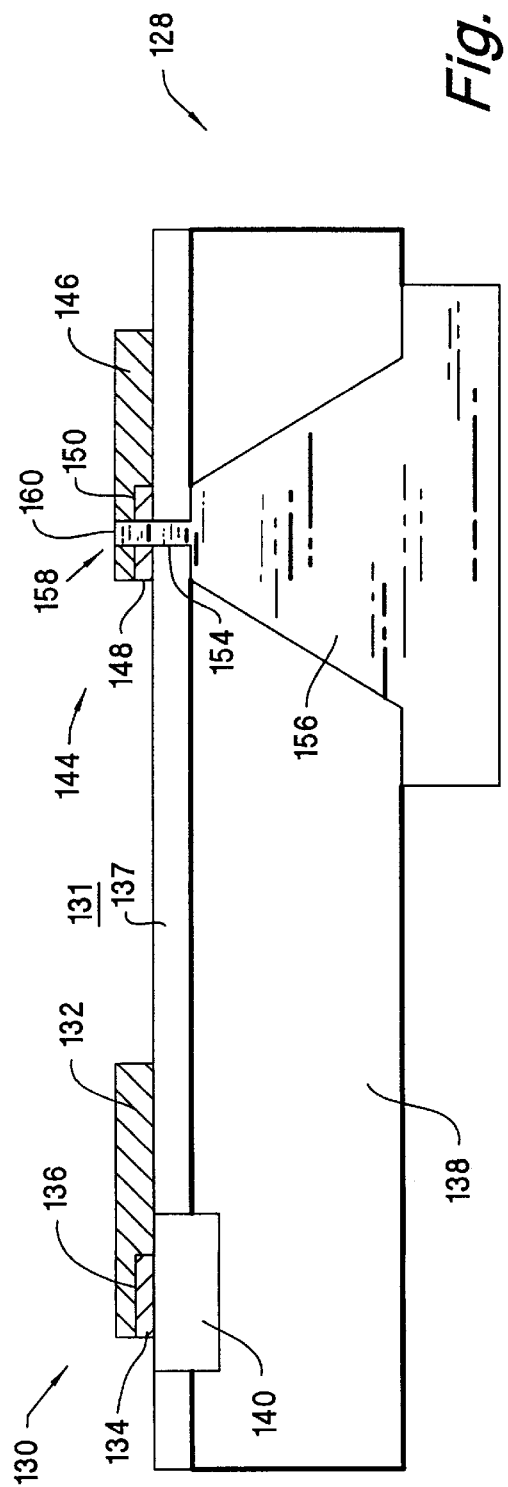

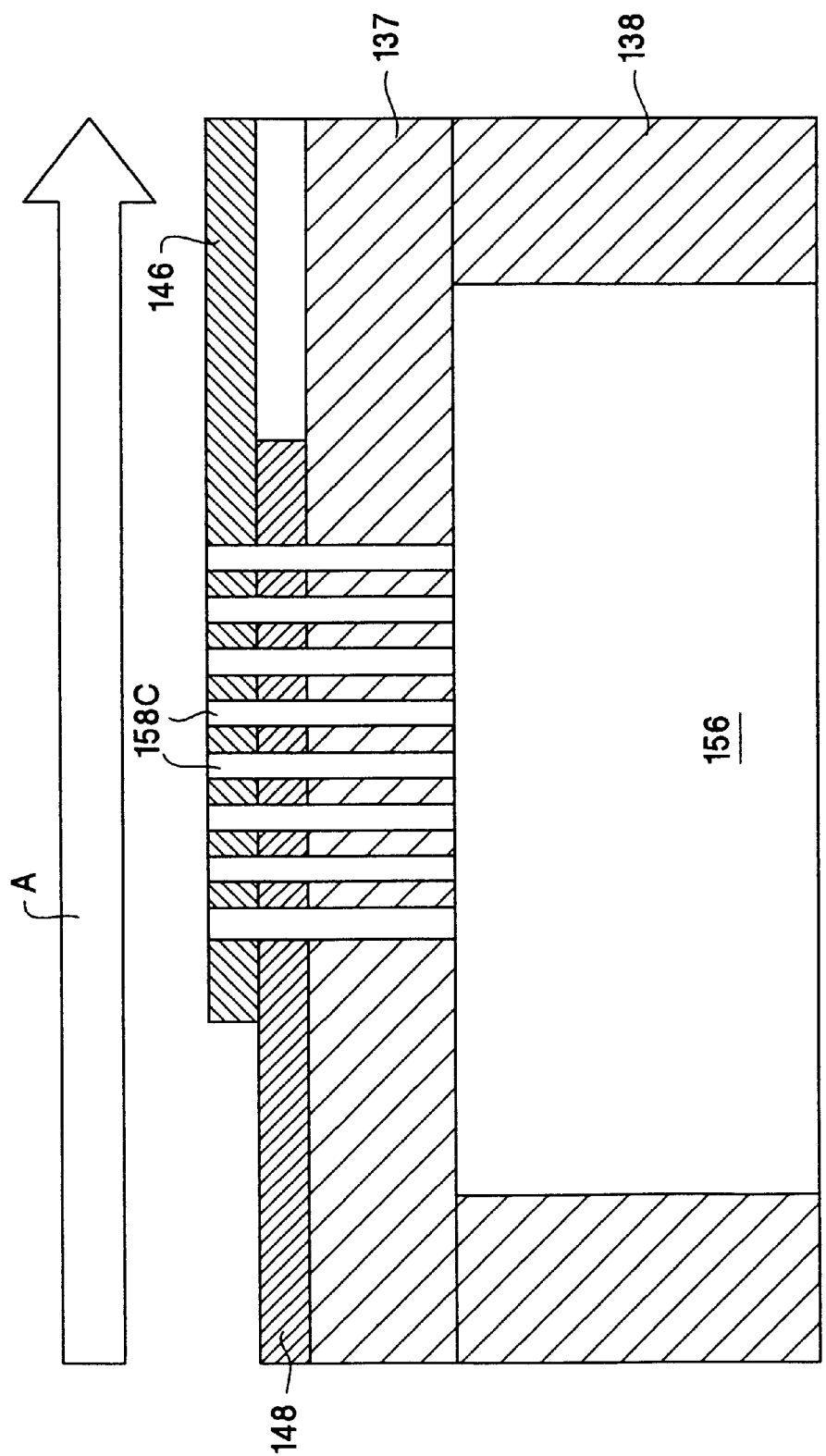

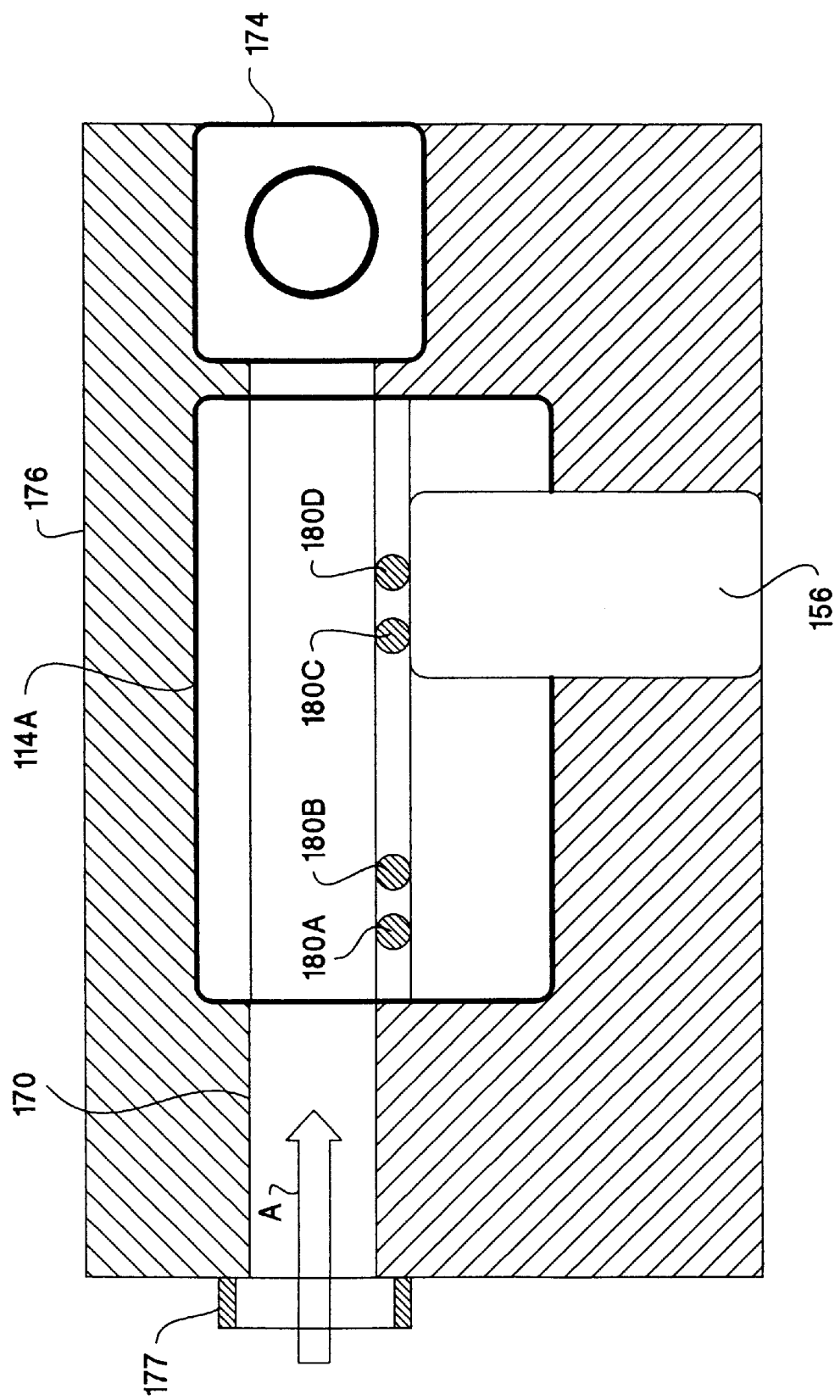

THERMOMETRIC VAPOR SENSOR WITH EVAPORATION SURFACE HAVING MICROPORES

FIELD OF THE INVENTION

The present invention is related to techniques for determining the concentration of a vapor in a gas stream and, more particularly, to apparatuses and methods for determining vapor concentration in a gas stream by measuring evaporative cooling in the gas stream.

BACKGROUND

The measurement of the concentration of a vapor in a gas is important in many situations. For example, it is useful to know the concentration of flammable gases in a gas stream in combustion technology. The humidity of air in an area is of interest to people concerned about the weather. In an organic chemical manufacturing facility, monitoring the concentration of vapors of certain volatile liquids in air is critical to the safety of the personnel in the area. Further, to assess the physiological condition of a patient in surgery, an anesthesiologist would want to know the concentration of an anesthetic in a gas stream administered to the patient. The concentration of water vapor in the exhaled air of a person can indicate the functioning condition of the person's respiratory system. The detection of temperature and moisture content of air being inhaled and exhaled will provide valuable information to health care professionals on aerosol therapy and toxicology of toxic gases inhalation.

Vapor concentration sensors based on measuring the mass of vapor absorbed on polymer films coated on surface acoustic wave devices have been developed. For example, Jay W. Grate and Mark Kluxty, *Anal. Chem.*, vol. 63, pp 1719–1727 (1991), describe a humidity sensor in which vapor absorption changes the frequency of oscillation of mass-sensitive resonators. Also, Polymer-based impedance effect humidity sensors are disclosed by S. Tsuchitani et al. in "A humidity sensor using ionic copolymer and its application to a humidity—temperature sensor module," *Sensors and Actuators*, Vol. 15, No. 4, pp 375–386, 1988. In the Tsuchitani humidity sensors, moisture absorption by ionic copolymers causes a change in impedance in an electrical circuit, thereby causing a change in oscillation frequency. However, vapor concentration sensors by vapor absorption are not very specific and are subject to interference by any absorbable vapor that has not been present in samples used for the calibration of the vapor absorption sensors. Moreover, such vapor sensors do not work well near the condensation point because they may not respond to a fall in humidity quickly. Therefore, a need exists for a highly specific vapor concentration sensor that will function over a wide range of concentrations.

Humidity sensors have been used for many years to determine air humidity for weather reporting. For such applications, one simple kind of humidity sensor has a dry bulb thermometer and a wet bulb thermometer. The wet bulb thermometer has a thermometer with a bulb moistened by a wick. Generally water passes by capillary action against gravity up the wick from a container. Water evaporates from the wick when the air is unsaturated with respect to water vapor. Due to the cooling effect of water evaporating from the wick, the temperature of the wet thermometer will be lower than the true temperature of the air had there been no evaporation. The temperature of the wet thermometer is known as the "wet-bulb temperature." The temperature that is measured by a dry thermometer, known as the "dry-bulb temperature," and the wet-bulb temperature are used to determine the humidity in air. See, for example, McCabe and Smith, *Unit Operations of Chemical Engineering,* McGraw-Hill, Ch. 24, 3rd ed., (1956). Such humidity sensors tend to be large. Their response time is typically not very fast.

More recently, moisture sensors employing micro-thermocouple sensors for determining temperature and relative humidity in airstream have been reported, for example, in "Design and development of a micro-thermocouple sensor for determining temperature and relative humidity patterns within an airstream," *J. Biomechan. Eng* Vol. 111, PP. 283–287, Nov. 1989. In such a device, a wet-bulb thermocouple junction is coated with a sprayed-on boron nitride coating, which is reported to be hard and porous. A sleeve is used to supply water to the boron nitride coating. It would appear that coating a thermocouple junction by spraying is not an easy task and one has to take special care to position the sleeve precisely to wet the boron nitride coating without leakage. It is also difficult to form a boron nitride coating that is stable on metal or glass surfaces. Moreover, to get a porous structure suitable for conducting water adequately one needs to form a boron nitride layer that is quite thick, making it brittle and slow to transfer heat.

Therefore, a need exists for a vapor concentration sensor that is relatively simple to construct, and particularly for a vapor concentration sensor that is sturdy. Recently, we reported a vapor sensor employing micropores, see U.S. patent application Ser. No. 08/878,566, "THERMOMETRIC APPARATUS AND METHOD FOR DETERMINING THE CONCENTRATION OF A VAPOR IN A GAS STREAM," filed on Jun. 19, 1997, Attorney Docket No. 10951173-1, which is incorporated by reference in its entirely herein. However, there is still a need for a vapor sensor that is rugged, simple to make, and can be produced in a small size.

SUMMARY

In one aspect, the present invention provides a sensor for sensing the concentration of a vapor of a vaporizable liquid in a gas stream. An embodiment of the sensor includes a micropore which has an opening into the gas stream. The micropore has an evaporation end at the opening into the gas stream and a lumen which conducts the vaporizable liquid from a supply of thy liquid to the opening for evaporation at the evaporation end. A wet-transducer temperature sensor (or simply "wet temperature sensor") capable of sensing temperature at the evaporative end of the micropore. The wet temperature sensor has a heat sensitive part in contact with the liquid in the micropore near the opening. That heat sensitive part circumscribes the micropore and forms part of the lumen. When the liquid evaporates, the latent heat of evaporation is absorbed from the gas stream and the surroundings thereof, resulting in the cooling of the vicinity of the wet temperature sensor. Such heat loss when the wet temperature sensor wet with the liquid is placed in the gas stream will result in the temperature sensed by the wet temperature sensor being lower than the non-evaporative temperature of the gas stream. This lowering in temperature can be measured to determine the concentration of the vapor in the gas stream.

To determine the lowering in temperature described above, in an embodiment, a dual-transducer temperature sensor is provided to compare the wet-transducer temperature to the gas stream temperature. In such a dual-transducer temperature sensor, a wet-transducer temperature sensor senses the temperature at the evaporative surface and a reference temperature sensor senses the gas temperature without evaporation as a reference.

In an embodiment, multiple micropores can be included to increase the area of evaporation such that steady state temperature can be achieved for determining the vapor concentration quickly. Due to the ability to form micropores of uniform size and shape, and to form small temperature sensors with thin layers of material, fast heat transfer can be achieved to enable fast response time for vapor sensing. Since the micropores are small, capillary action can hold the liquid in the micropores even when the temperature sensors are turned in different orientations. Thus, with the present invention, a fast vapor concentration sensor can be made, even for applications that require small dimensions and independence to the position relative to gravity.

The sensor of the present invention is advantageous over conventional sensors with woven wicks. First, regarding woven wicks, it is difficult to form a woven material that can wrap uniformly around a temperature sensitive unit such as a thermistor head or thermocouple junction to provide adequate liquid without dripping. Also, there may be a tendency for fibrous material to become unwoven and come off, which is not desirable in certain applications, such as in an airway of a patient. Similarly, materials that are brittle and fragile, such a boron nitride, may flake off, which would lead to undesirable patterns of heat and mass transfer as well. In conventional wick-type humidity sensors, water is drawn against gravity by capillary action through a fibrous wick from water in a container to a thermometer. This is not conducive for using the humidity sensor in hard-to-reach places since the water container and the wick render the wet-bulb thermometer hard to position. A wickless embodiment of a vapor concentration sensor according to the present invention can be used in hard-to-reach places such as the airway of a patient. As used herein, the term "wickless" means the lack of a fibrous material that conducts liquid by capillary action against gravity from a liquid container.

Sensors can be made according to the present invention to be highly specific to the vapor for which the concentration information is desired. For example, an alcohol vapor concentration sensor can be made by providing micropore(s) in contact with a wet-transducer temperature sensor with alcohol. Such a vapor concentration sensor will operate well to measure the concentration of alcohol in a gas stream despite the presence of other vapors in the gas stream. The driving force for the evaporation of alcohol at the wet junction is independent of the vapor pressure of other volatiles in the gas stream. Such specific sensors are advantageous over absorption vapor concentration sensors because the rate of vapor absorption of such absorption vapor concentration sensors is affected by the presence of other vapors in the gas. Another advantage of the sensor of the present invention is that a vapor sensor can be made for sensing a few different vapors, by having micropores that conduct different liquids from reservoirs to different wet-transducer temperature sensors.

A further advantage of the apparatuses of the present invention is that they can be manufactured easily, using automated systems and for mass production. Many components of the apparatuses can be made by layering of materials and processing the layers in ways similar to processes used in manufacturing integrated circuits. By using such processes, vapor sensors of very small sizes can be made. Such small size vapor sensors can be used in various applications, ranging from physiological monitoring to the control of equipment the performance of which is affected by the presence or concentration of certain vapors. As an example, the rate of drying a material wet with water is sensitive to the water humidity of the air in which the drying takes place.

BRIEF DESCRIPTION OF THE DRAWINGS

The following figures are included to better illustrate the embodiments of the apparatus and technique of the present invention. In these figures, like numerals represent like features in the several views.

FIG. 1 shows an embodiment of a vapor concentration sensor according to the present invention.

FIG. 2A shows a plan view of a dual-transducer temperature sensor that can be used for the vapor sensor of FIG. 1.

FIG. 2B shows a sectional view of a dual-transducer temperature sensor shown in FIG. 2A.

FIG. 3C shows a sectional view in portion of a wet-transducer temperature sensor having multiple micropores similar to that of FIG. 3A and FIG. 3B, having an orientation perpendicular to FIG. 3A and FIG. 3B.

FIG. 8B shows a sectional view of the portion of the apparatus shown in FIG. 8A.

FIG. 9A shows a sectional view of a tubular thermocouple junction according to the present invention.

FIG. 9B shows a sectional view of a portion of the thermocouple junction shown in FIG. 9A.

DETAILED DESCRIPTION OF THE INVENTION

Figure 2C:
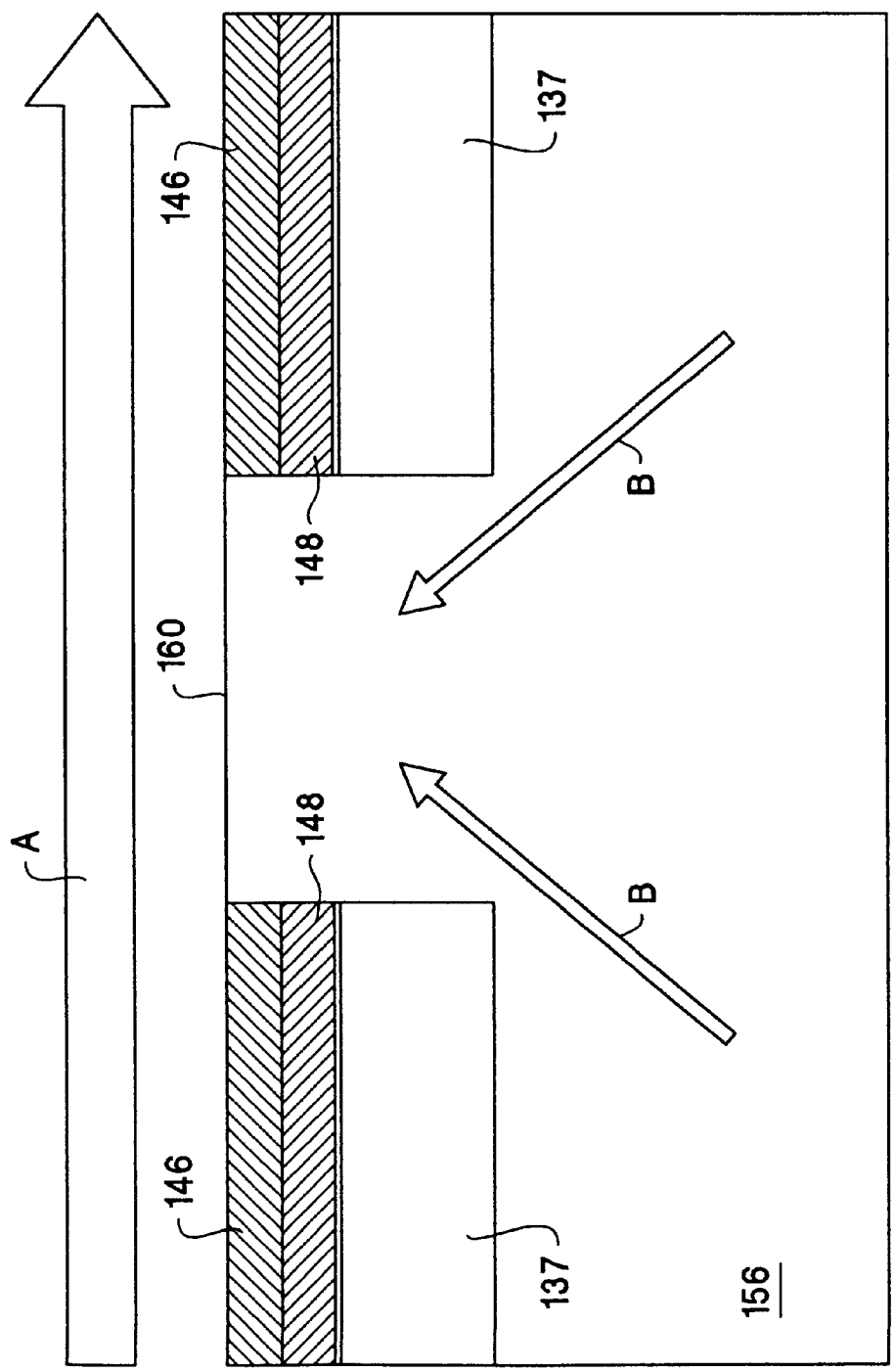
FIG. 2C shows a sectional view of a portion of a wet-transducer temperature sensor of the dual-transducer temperature sensor shown in FIG. 2A.

In one aspect, the present invention provides a technique for vaporizing a liquid from a micropore such that the decrease in temperature due to the absorption of latent heat of evaporation at the evaporation surface can be measured to determine the concentration of a vapor of the liquid in a gas.

FIG. 1 shows an embodiment of a vapor sensor of the present invention for determining the presence or concentration of the vapor of a volatile liquid in a gas. The vapor sensor (or apparatus) 100 has a "dual-transducer temperature sensor" 114 connected by means of an electrical cable 116 to a processor 118 for processing the temperature data from the dual-transducer temperature sensor 114 to indicate the vapor concentration in the gas. The humidity (or concentration of the vapor) can be displayed in a display device 120 such as a computer monitor, liquid crystal display, light emitting diode display, paper printer, plotter, galvanometer with a indicator needle, and the like. As used herein, the term "dual-transducer temperature sensor" refers to a sensor having two different transducers—one for sensing the temperature of a liquid with steady state heat loss in the gas stream due to evaporation of the liquid, and one for sensing the temperature of the gas stream without evaporation. This allows the difference between the two temperatures to be determined. It is to be understood that a sensor is considered to be such a dual-transducer temperature sensor if such a sensor has two transducers having temperature-dependent properties (e.g., resistance or voltage difference, from which vapor concentration can be determined), which can be measured such that such a temperature difference can be derived from the properties, even though the temperatures may not need to be explicitly calculated.

The dual-transducer temperature sensor 114 has a reference temperature sensor 130 for sensing the temperature of the gas and a wet-transducer temperature sensor 144 for sensing the temperature of a liquid, which will lose vapor molecules to the gas by vaporization to the extent dependent on the degree of unsaturation of the vapor of the liquid in the gas. As used herein the term "wet-transducer temperature sensor" refers to a temperature sensing device, typically electrical, that is used to measure the temperature of the liquid in contact with the temperature sensor wherein the liquid loses vapor by evaporation to the gas contacting the liquid. As a result, the vicinity of the evaporation surface cools to a steady state temperature lower than that of the bulk gas (i.e., the bulk of the gas stream whose temperature is not significantly affected by the evaporation) due to the latent heat of evaporation.

FIGS. 2A and 2B shows an embodiment of a dual-transducer temperature sensor that can be used for the vapor sensor of FIG. 1. In this embodiment, the dual-transducer temperature sensor 128 has a reference thermocouple 130 exposed to the gas stream 131 for measuring the reference temperature of the gas in the gas stream 131. In this embodiment, the thermocouple 130 is not wetted by a liquid, thus its temperature can be referred to as the "dry-transducer temperature." The thermocouple 130 is composed of a first dry-transducer metal layer 132 and a second dry-transducer metal layer 134 forming a dry-transducer thermocouple junction 136 where the layers 132, 134 contact each other.

Wires (not shown in FIG. 2) connected to the thermocouple 130 can be used for transmitting electrical signal representing temperature to the processor 118 (i.e., connecting to the first dry-transducer metal layer 132 and the second dry-transducer metal layer 134). In a thermocouple, the voltage difference across the thermocouple junction 136 develops depending on the temperature of the thermocouple junction. This voltage difference can be measured to determine the temperature experienced by the thermocouple junction 136. The thermocouple 130 is supported by a thermal insulator 137, which in turn is supported by a substrate 138. Preferably, the area of the thermocouple about the thermocouple junction 136, which is the heat sensitive part of the thermocouple, is situated on a gap 140. The gap 140 can be formed (e.g., by chemical etching or laser ablation) from the substrate 138 and thermal insulator 137. The gap 140 can be made to be open to the gas stream 131 to provide increased contact surface area by the gas stream near the thermocouple junction 136 to facilitate heat transfer from the gas stream to the thermocouple junction 136. Alternatively, the gap 140 may be narrow enough so that the thermocouple junction entirely covers it on the insulator 137.

In the neighborhood, or vicinity, of the reference thermocouple 130 is a "wet-transducer" temperature sensor, in this case a wet-transducer thermocouple 144. The wet-transducer thermocouple 144 also has two metal layers, i.e., a first wet-transducer metal layer 146 and a second wet-transducer metal layer 148, forming a wet-transducer thermocouple junction 150 therebetween. The wet-transducer thermocouple 144, exposed to the gas stream during vapor sensing, is also supported by the thermal insulator 137. A micropore 154 passes through the thermal insulator 137 and the wet second metal layer 148 and the wet first metal layer 146, providing fluid communication from a fluid reservoir 156 to an opening 158 into the gas stream 131. The liquid evaporates from a surface 160 in the opening 158. Heat loss due to the latent heat of evaporation lowers the temperature at the opening 158 than that sensed by the dry reference thermocouple 130. It is to be noted that the heat insulator layer 137 is optional. In a case without a heat insulator layer, the substrate 138 can support the thermocouples 130, 144 directly, and micropore 154 can pass through the substrate and the wet-transducer thermocouple metal layers 146, 148.

As liquid evaporates from the opening 158, replacement liquid can migrate from the liquid reservoir 156 via the micropore 154 to the evaporation surface 160, by capillary force, for example. Preferably, the heat sensitive part (i.e., thermocouple junction 150) circumscribes a section of the micropore 154 near to the opening 158 to provide increased heat transfer from the liquid in the micropore 154 to the wet-transducer thermocouple junction 150. The migration of liquid is preferably adequate to maintain the liquid evaporation near to the opening 158 substantially constant for a period adequately long for the temperature of the wet-transducer thermocouple 144 to come to a steady state temperature after the dual-transducer temperature sensor 128 is put into a gas stream to sense the presence or quantity of a vapor in the gas stream. Wires (not shown in the figures) can be used to connect the wet-transducer thermocouple 138 to electronics for determining the temperature thereof or for comparing with data collected from the dry thermocouple 130.

FIG. 2C shows in more detail the micropore 154 and the evaporation surface 160 thereof. Arrow A shows the flow of gas in the gas stream. Arrows B show the replacement liquid flowing toward the evaporation surface 160 through the micropore 154. Although the application of the present invention is not dependent on any particular scientific theory, it is believed that a boundary layer of gas saturated with the vapor exists at the evaporation surface 160. The concentration of the vapor gradually decreases with the distance from the evaporation surface 160. Mass transfer in evaporation from a liquid surface in a gas stream has been extensively studied and is well understood by one skilled in the chemical engineering principles.

It is preferred that the micropore will have adequate capillary force to draw liquid from the liquid reservoir 156 to the opening 158 without being rate limiting. Preferably, as the liquid evaporates from the opening 158, adequate amount of liquid can flow (e.g., by capillary force) from the liquid reservoir 156 to allow the wet-transducer thermocouple 144 to come to a steady state temperature once placed in a desired location. For example, in the case of a humidity sensor, under normal operating conditions of the vapor sensor 100, between about 1° C. and 45° C. for relative water humidity of about 1% to 100% saturation, being not water-mass-transfer-limited, the micropore 154 will have a higher rate of evaporation at a lower relative humidity in the gas stream than at a higher relative humidity at the same dry temperature. The reference thermocouple 130 and the wet-transducer thermocouple 144 are held in close proximity of each other by the thermal insulator 137 and the substrate 138 such that they sense the temperature of gas portions that are close enough to have essentially the same pre-evaporation temperature and humidity. Typically, the reference thermocouple 130 is located upstream of the wet-transducer thermocouple 144 so that the reference thermocouple will not be affected by liquid evaporation.

Figure 3A:
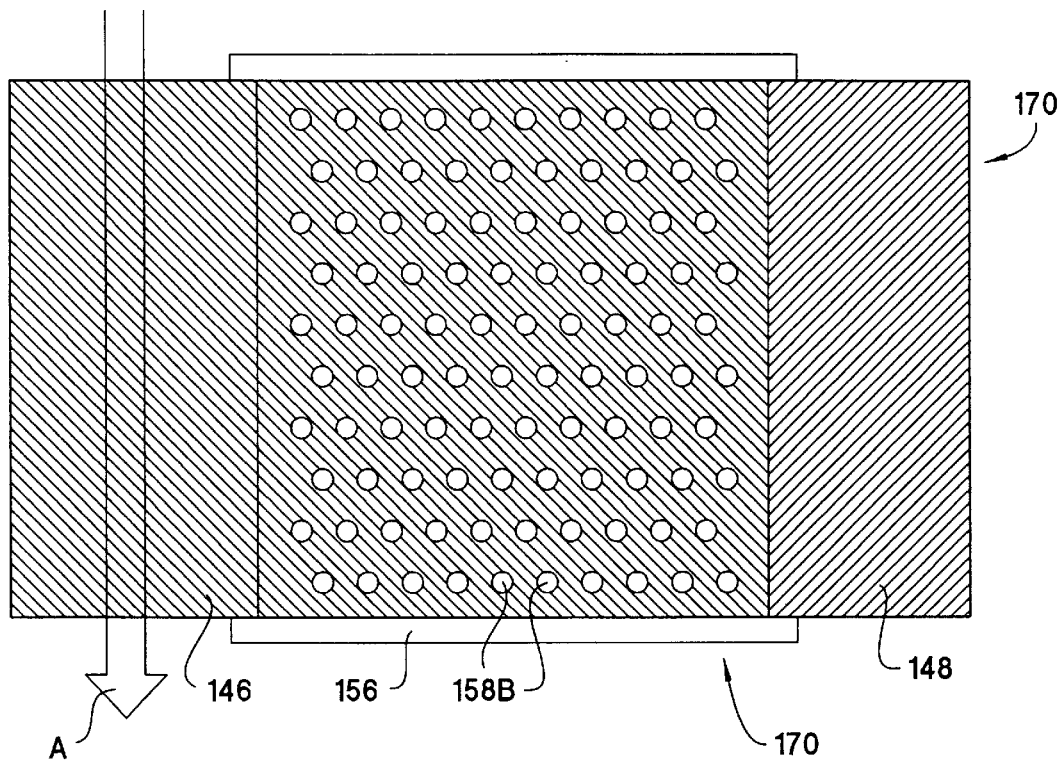
FIG. 3A shows a plan view in portion of a wet-transducer temperature sensor having multiple micropores according to the present invention.
Figure 3B:
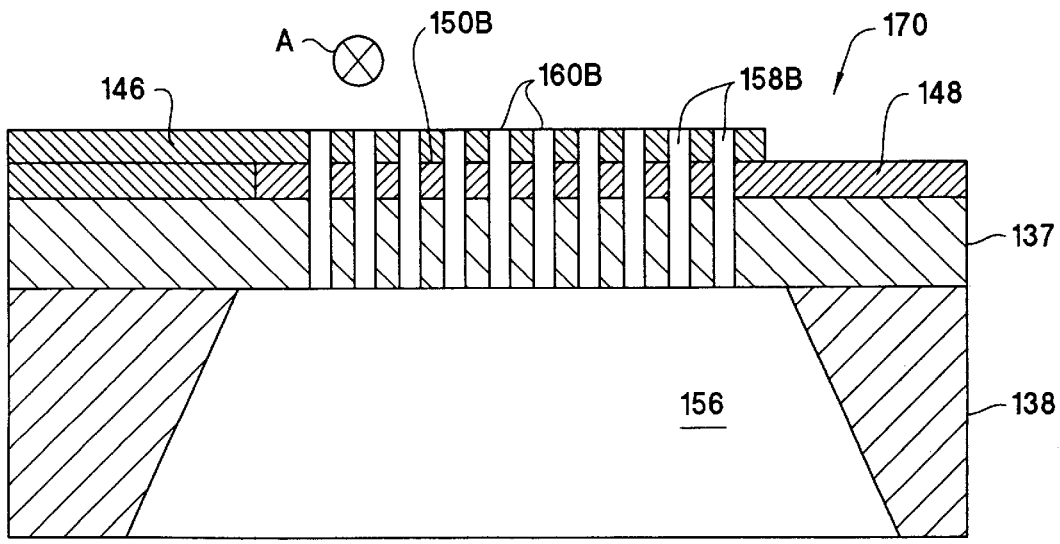
FIG. 3B shows a sectional view in portion of the wet-transducer temperature sensor of FIG. 3A.

Another embodiment of the sensor for determining vapor concentration in a gas is shown in portion in FIGS. 3A and 3B. In these figures, the arrow A shows the direction of flow in the gas stream. In this embodiment, the wet temperature sensor includes a plurality of micropores 158B are each connected to the liquid reservoir 156 for supplying the liquid to the openings of the micropores 158B for evaporation. The micropores 158B pass through a thermocouple junction 150B to the openings 160B. Such a plurality of micropores will provide a larger ratio of evaporating surface area to thermocouple junction area, thereby enabling the heat transfer to achieve a steady state faster for any change in the characteristics of gas stream. FIG. 3C is a sectional view of another embodiment similar to that of FIGS. 3A and 3B, except with a different number of micropores 158C and the sectional view is equivalent to one perpendicular to those of FIGS. 3A and 3B.

Figure 4A:
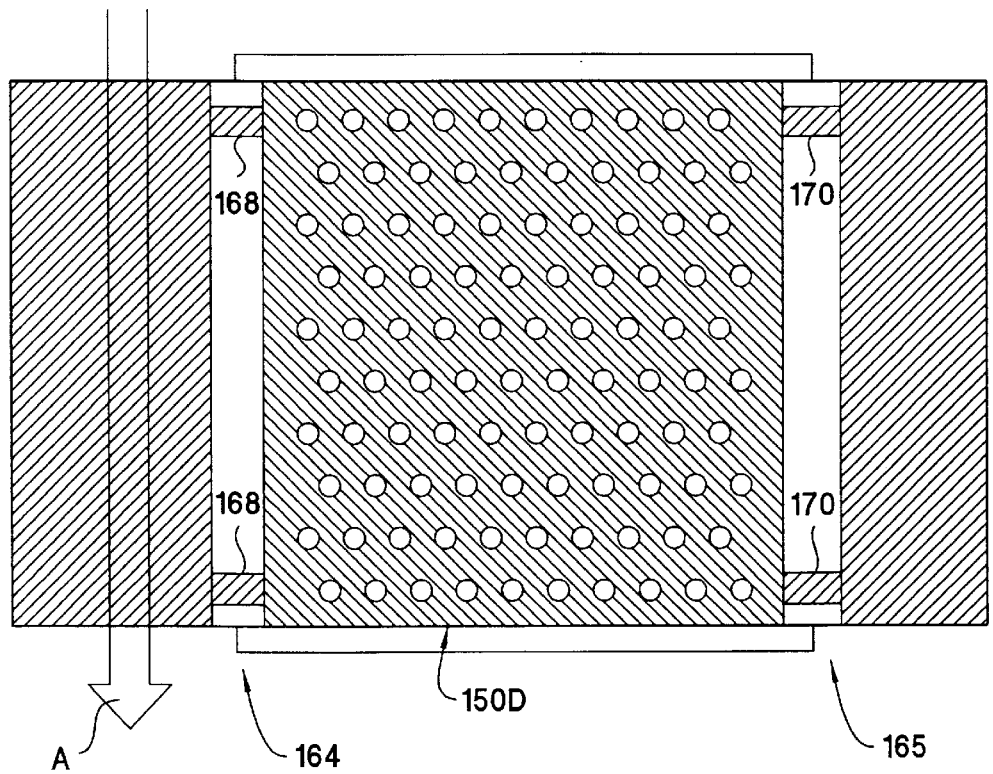
FIG. 4A shows a plan view in portion of another embodiment of a wet-transducer temperature sensor having multiple micropores according to the present invention.
Figure 4B:
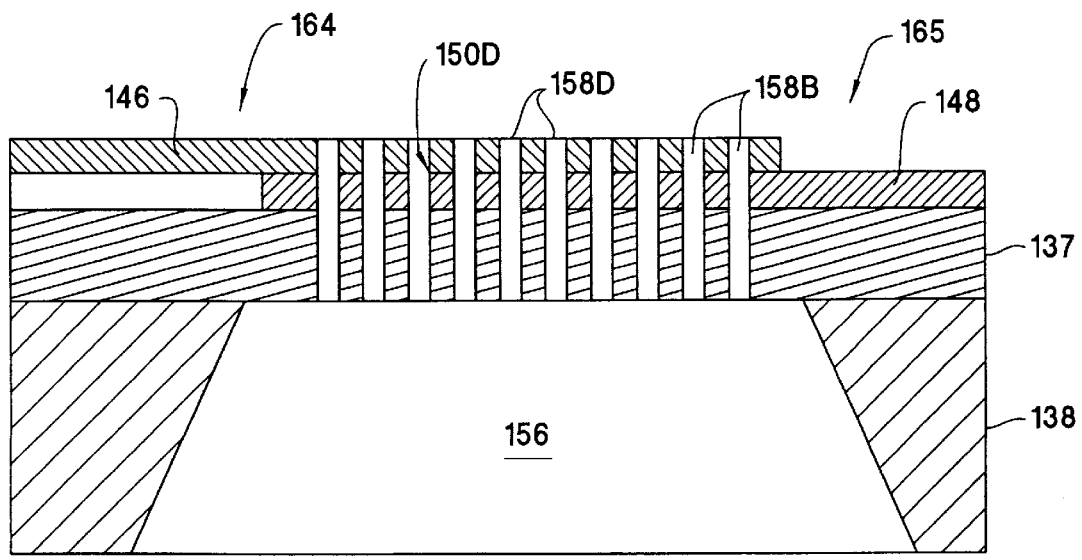
FIG. 4B shows a sectional view in portion of the wet-transducer temperature sensor of FIG. 4A.

FIGS. 4A and 4B show another embodiment with multiple micropores connected to the same liquid reservoir. In this embodiment, the metallic materials, which are thermal conductors, that connect the thermocouple junction 150D to other electronics is reduced to decrease the amount of heat transfer that is not originated from the evaporation from the micropores. In the regions 164, 165 outside the area of the thermocouple junction 150D having micropores 158D, the "wet" first metal layer 146 and the "wet" second material layer 148 are reduced in size to become bridges 168, 170 to reduce heat transfer therethrough. In this way, the isolation of the thermocouple junction region of the wet-transducer temperature sensor from undesirable external influence is improved.

Figure 5A:
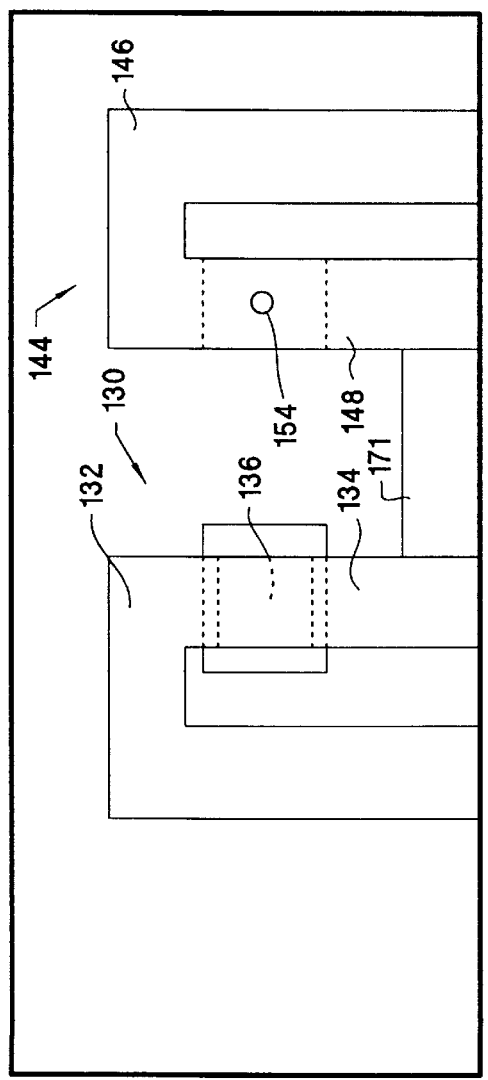
FIG. 5A shows a plan view of another embodiment temperature sensor, having a conductor bridge between the transducers of the dual-transducer temperature sensor.
Figure 5B:
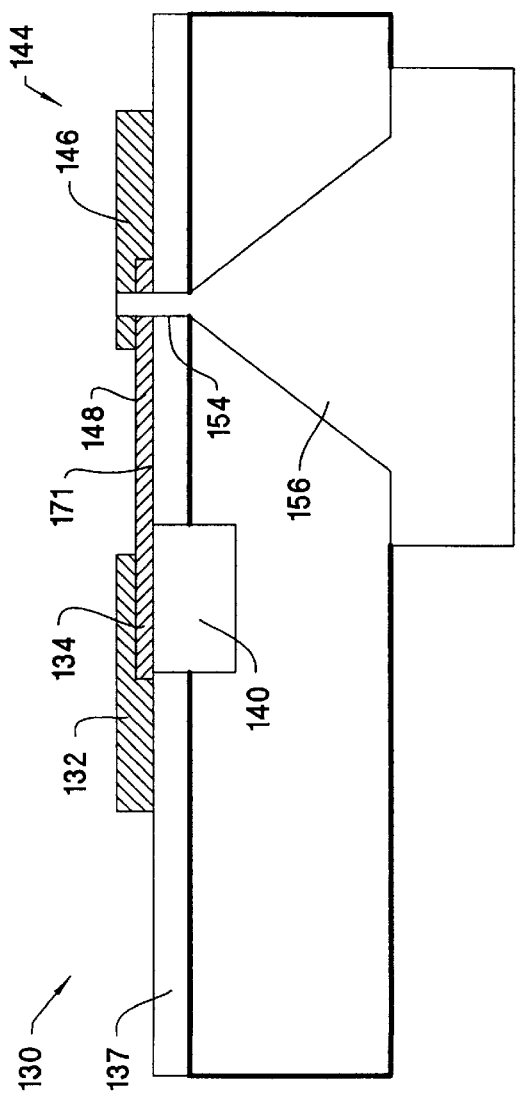
FIG. 5B shows a sectional view of the dual-transducer temperature sensor shown in FIG. 5A.

Although it is useful to obtain the temperature of the gas stream with the reference temperature sensor and the temperature with evaporative heat loss from the liquid in the micropore literally, the concentration or presence of a vapor in the gas stream can be conveniently determined by merely measuring the difference in electrical property between the dry transducer and the wet transducer without actually determining these temperatures numerically. In FIGS. 5A and 5B, the second wet-transducer metal layer 148 of the wet-transducer thermocouple 144 is in electrical contact with the second dry-transducer metal layer 134 through the bridge conductor 171. Preferably, the second dry-transducer metal layer 134, the bridge conductor 171, and the second wet-transducer metal layer 148 are all made of the same metal, thus obviating the problem of having to determine the voltage difference due to temperature change on a junction between these second metal layers 134, 148. Further, it is preferred that the first dry-transducer metal layer 132 and the first wet-transducer metal layer 146 are made of the same metal, which would significantly reduce the complexity of the manufacturing process. With this arrangement, to determine the difference between the temperatures measured by the dry-transducer reference thermocouple 130 and the wet-transducer thermocouple 144, only the voltage between the first wet-transducer metal layer 146 and the first dry-transducer metal layer 132 need to be measured. Thus, the temperature difference between the wet-transducer thermocouple 144 and the dry-transducer thermocouple 130 can be measured with only two conductor leads, since no conductor lead is needed for the second dry-transducer metal layer 134 or the second wet-transducer metal layer 148.

Figure 6A:
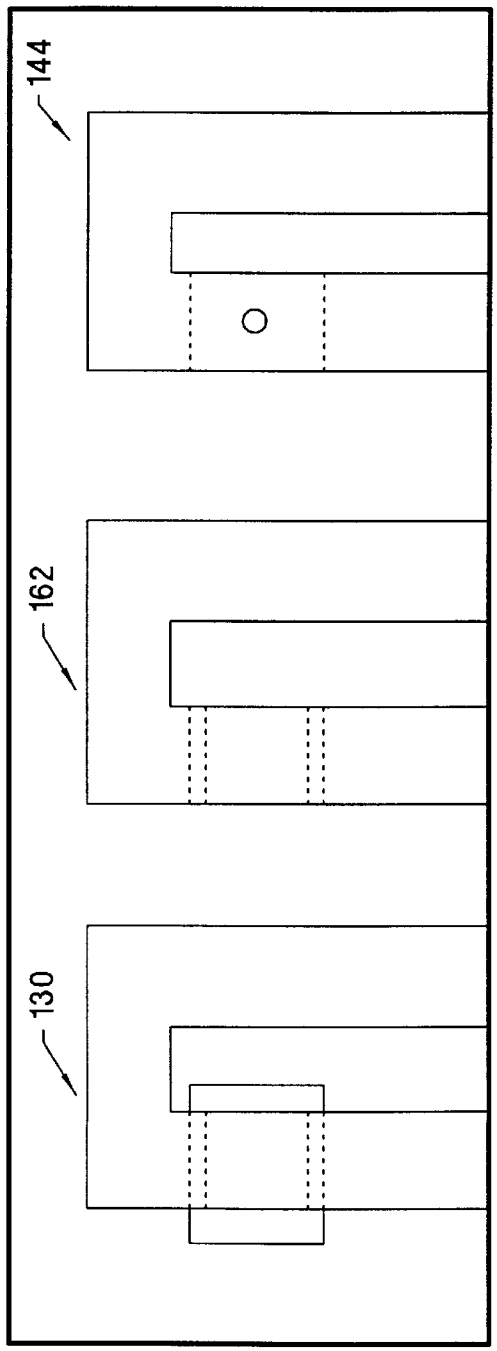
FIG. 6A shows a plan view of a portion of an apparatus according to the present invention, including a temperature sensor for sensing the solid support temperature.
Figure 6B:
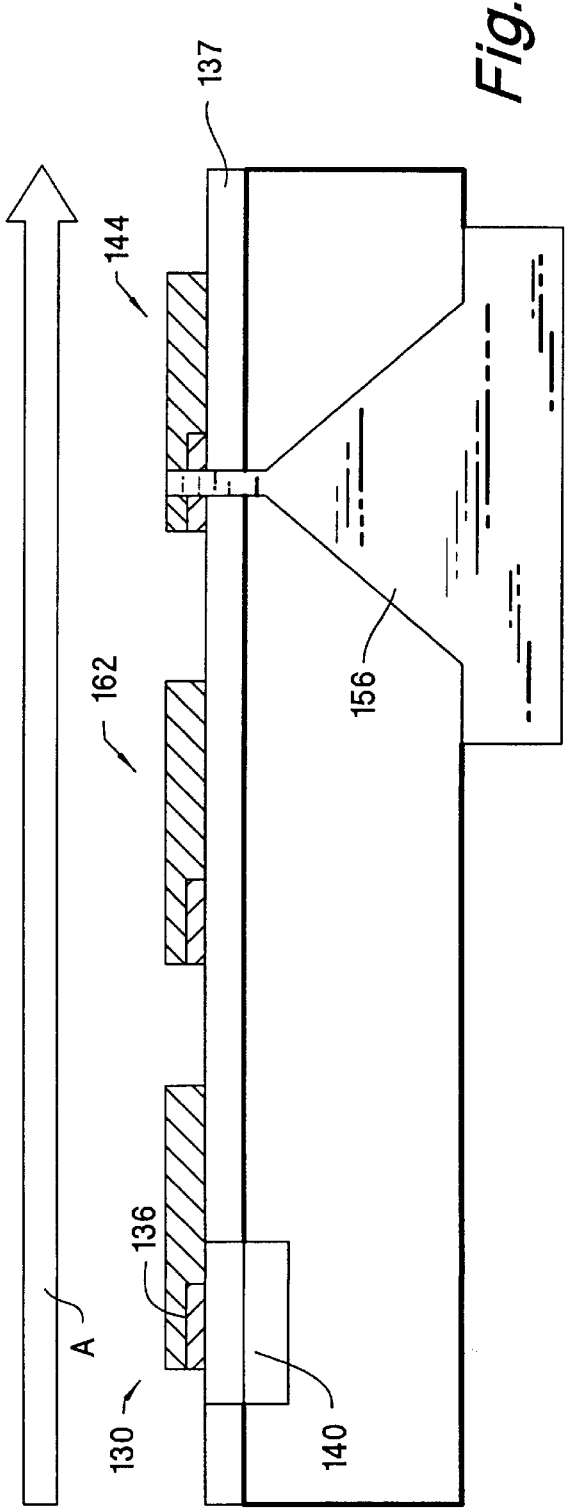
FIG. 6B shows a sectional view of the portion of apparatus shown in FIG. 6A.

In an alternative embodiment shown in FIGS. 6A and 6B, in additional to the wet-transducer thermocouple 144 and the dry-transducer reference thermocouple 130 similar to those described above, there is also a solid contact thermocouple 162 that senses the temperature of the solid support in contact with the dry-transducer reference thermocouple 130 and the wet-transducer thermocouple 144. As previously described, the dry-transducer reference thermocouple 130 preferably has a gap 140 under the thermocouple junction 136 to facilitate heat transfer from the gas stream A to the thermocouple junction 136. In contrast, the solid contact thermocouple 162 is preferably in direct contact with the support layer (in the case of FIG. 6, the thermal insulator 137 so that any difference between the air stream temperature and the support layer temperature can be measured and compensated for in the vapor concentration determination. The solid contact thermocouple 162 preferably contains a first metal layer and a dissimilar second metal layer, which can be the same materials as the first and second metal layer in either the dry-transducer thermocouple 136 or the wet-transducer thermocouple 144.

Figure 6C:
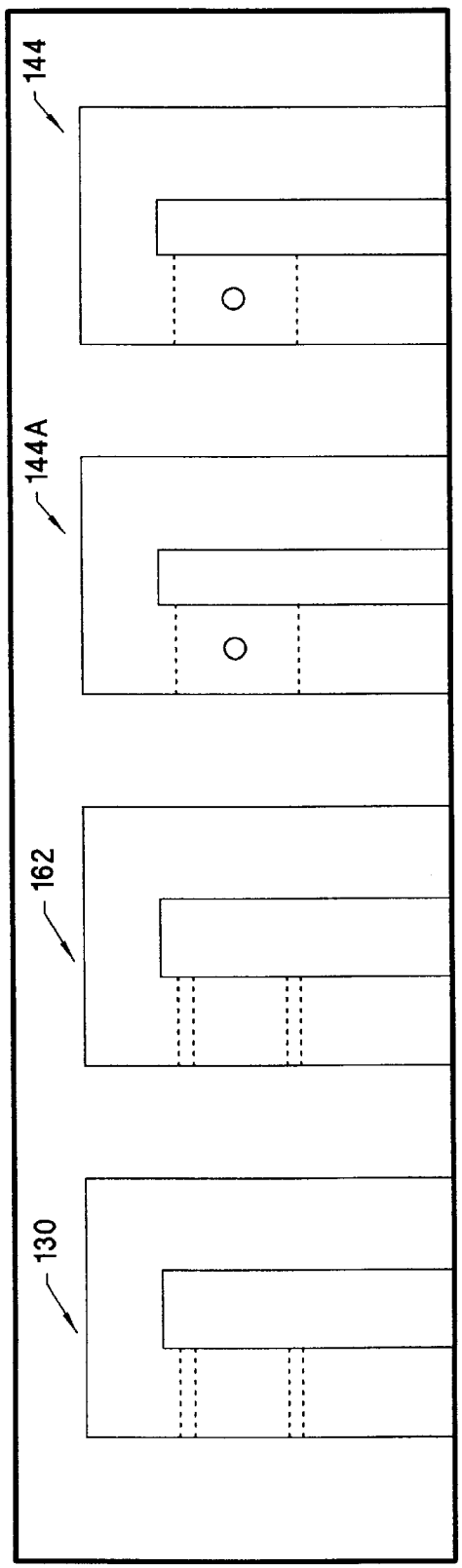
FIG. 6C shows a plan view of a portion of an apparatus according to the present invention, including multiple temperature sensors for sensing temperature of evaporative surfaces of different liquids.
Figure 6D:
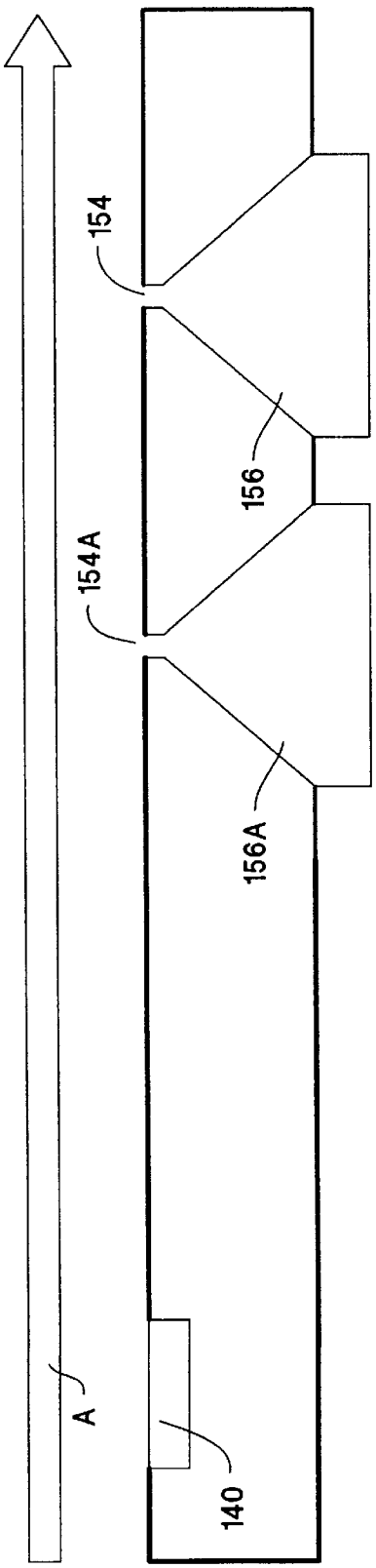
FIG. 6D shows a sectional view of the portion of apparatus shown in FIG. 6C.

FIG. 6C and FIG. 6D show another embodiment of a vapor sensor in which two different vapors can be sensed. In this sensor, a first liquid reservoir 156 can contain a first liquid. This first liquid will be evaporated from a first micropore 154 into the gas stream A at a first wet-transducer thermocouple 144. A second liquid will be evaporated from a second liquid reservoir 156A into the gas stream A from a second micropore 154A at a second wet-transducer thermocouple 144A. A dry reference thermocouple 130 measures the gas stream temperature without evaporation and a solid contact thermocouple 162 measures the temperature of the solid support of the thermocouples. For clarity, in FIG. 6D, the details structures of the thermocouples and support structures are not shown.

Figure 7A:
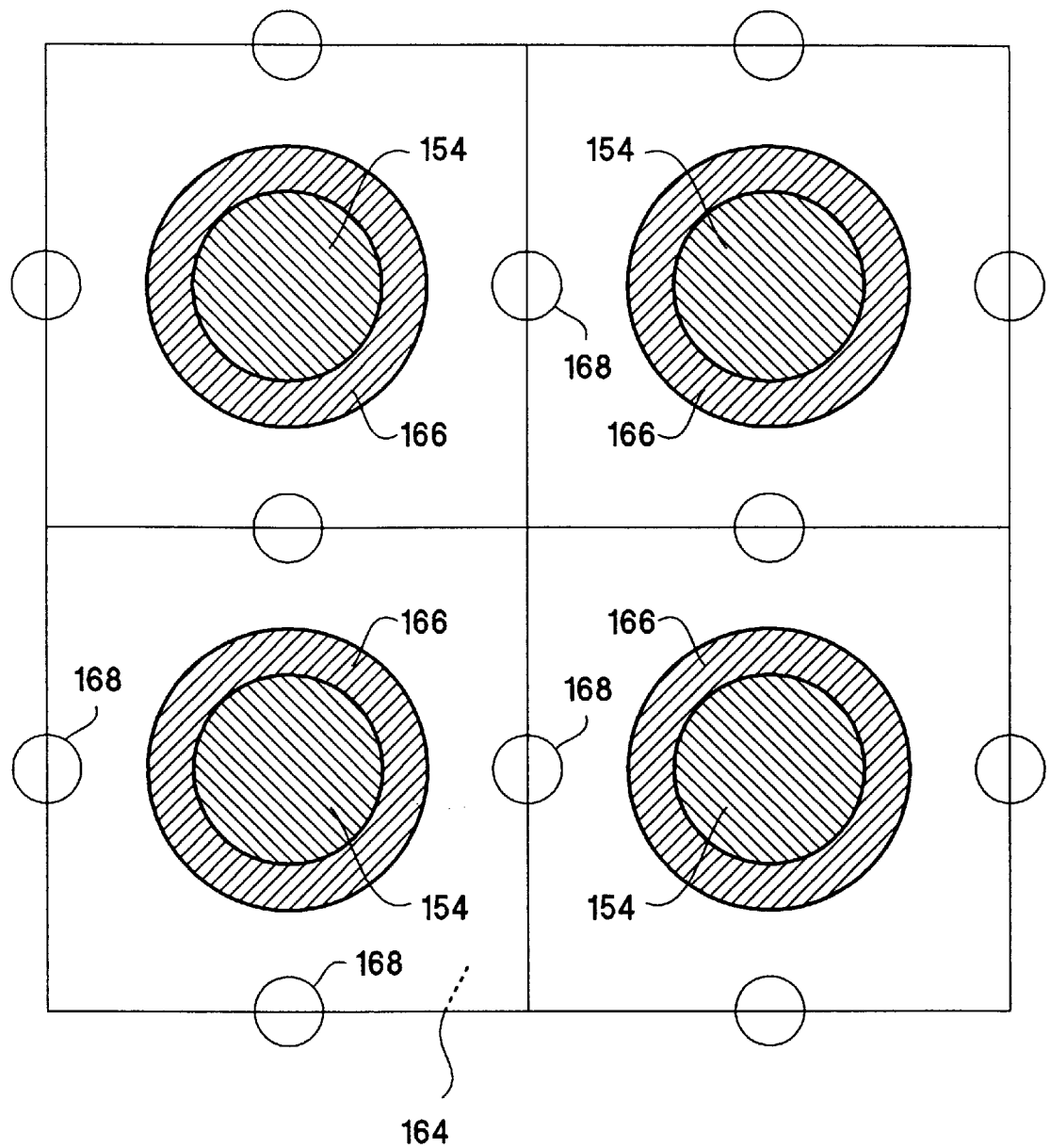
FIG. 7A shows a plan view of a portion of an apparatus according to the present invention, including wet temperature sensors having air gaps for thermally insulating temperature sensing elements.
Figure 7B:
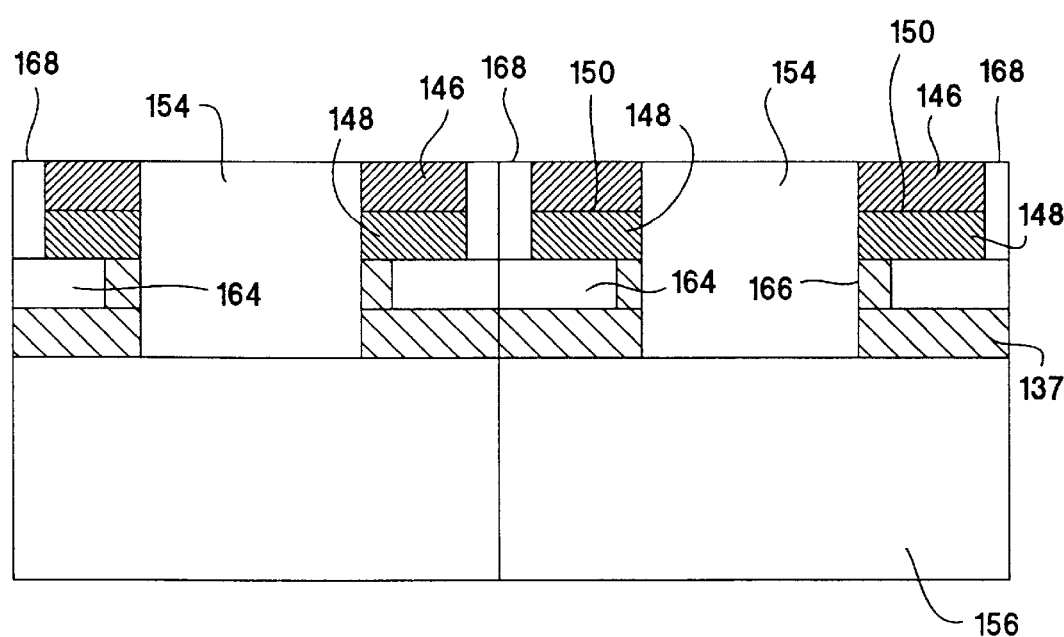
FIG. 7B shows a sectional view of in portion of the apparatus shown in FIG. 7A.

To further reduce the effect of conductive heat transfer from solid structures near the micropore, even better heat insulation than the thermal insulator layer 137 can be provided. FIGS. 7A and 7B show in plan view gaps 164 interposing between the thermal insulator layer 137 and the wet-transducer thermocouple junction 150 over substantial areas around the micropores 154, with the exception of the luminal wall 166. The gap 164 can be filled with gas from the gas stream that is being sensed. Vents 168 open to the gas stream permit the gas to fill the gaps 164. Alternately, the gap 164 can be filled with a different gas (e.g., one with lower thermal conductivity or heat capacity) and the vents sealed to trap that gas in the gap 164.

Figure 8A:
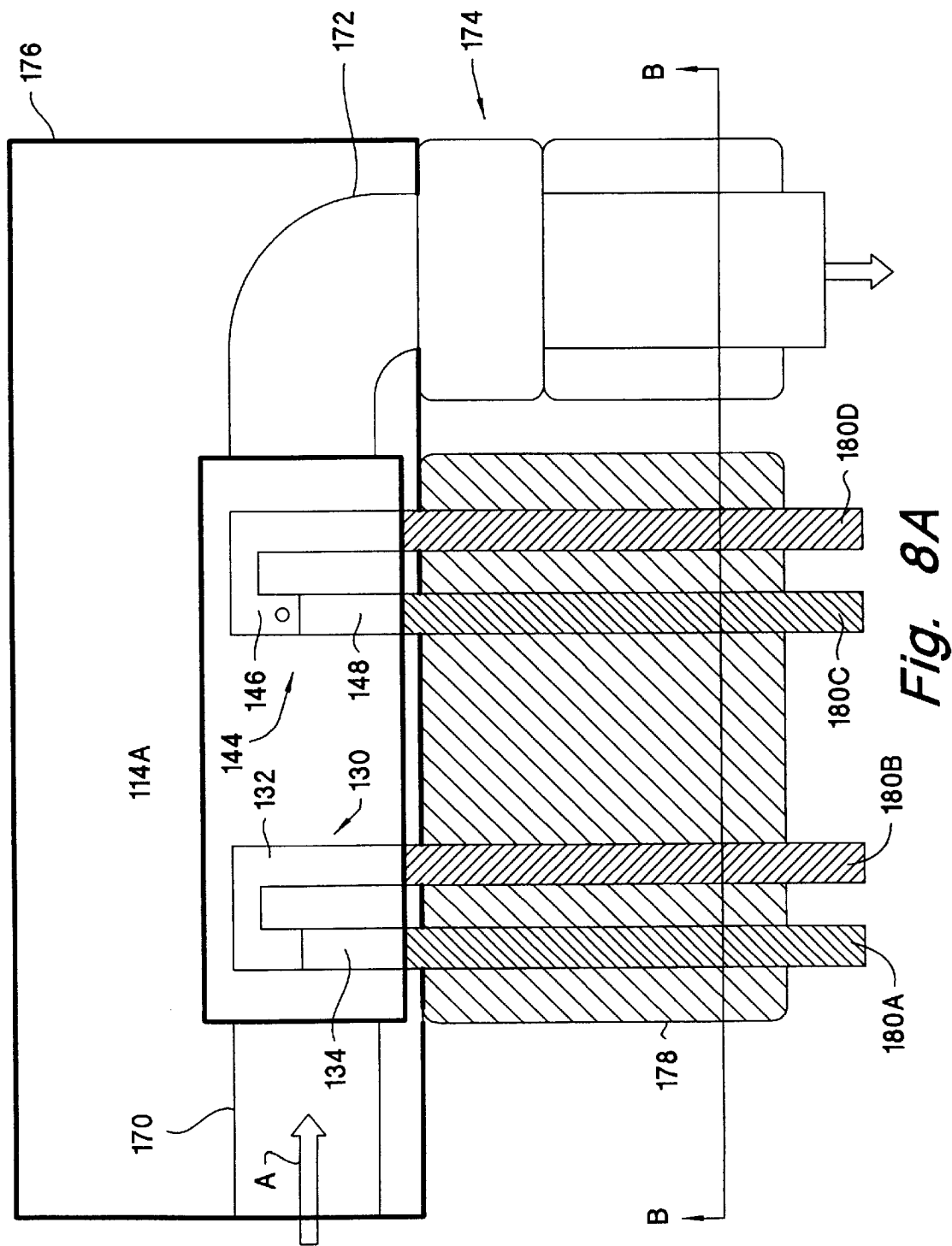
FIG. 8A shows a plan view of a portion of an apparatus according to the present invention, including a connectors for connecting temperature sensors to gas flow and to electronics.
Figure 8C:
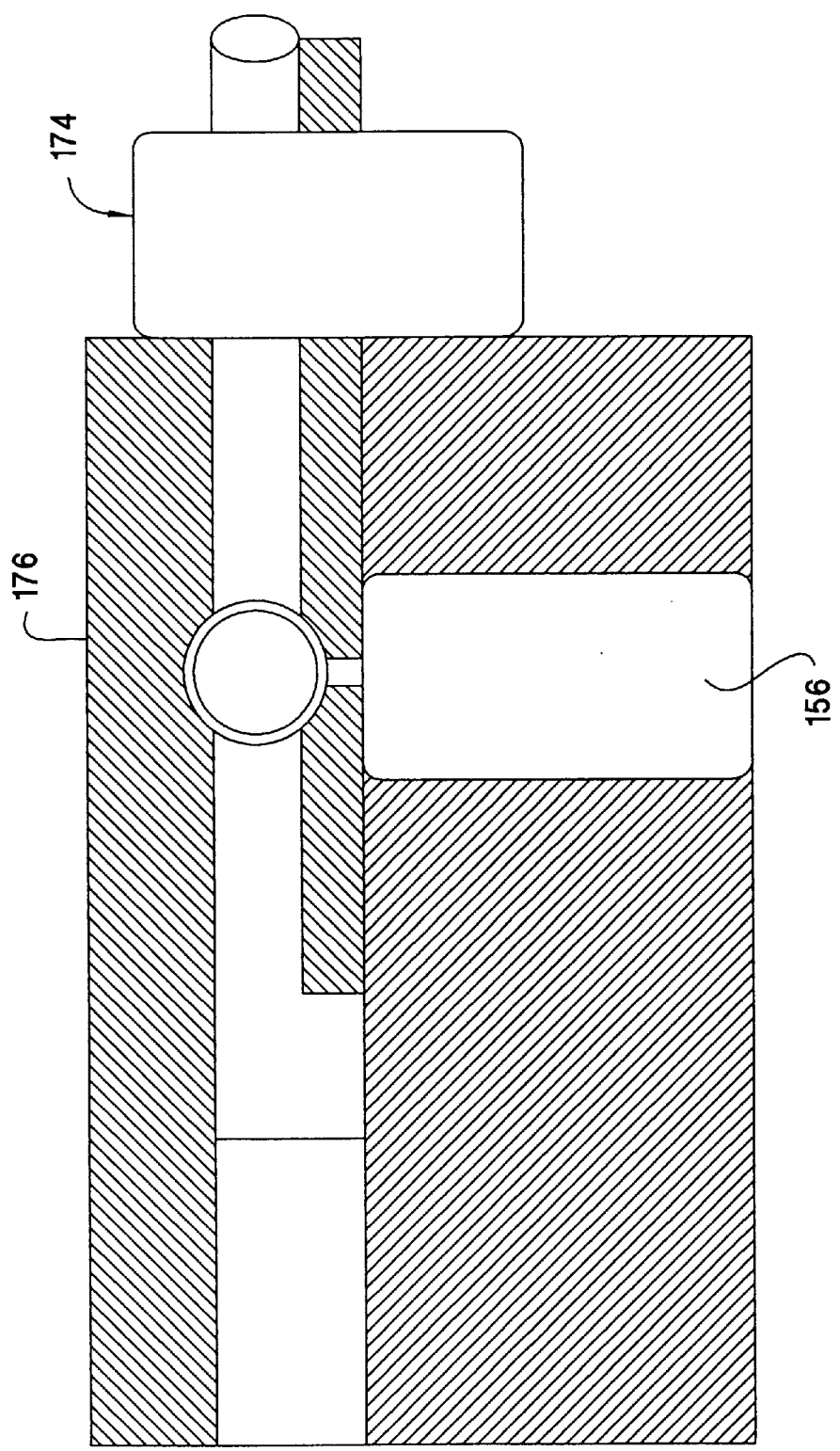
FIG. 8C shows a sectional view of a portion of the apparatus shown in FIG. 8A and FIG. 8B, oriented at right angle thereto.

FIGS. 8A and 8B show an apparatus in which the dual-transducer temperature sensor described above is used in conjunction with connecting structures. As shown, a dual-transducer temperature sensor 114A is disposed in the path of a gas stream A in a gas flow channel 170. The exit end 172 of the gas flow channel 170 is connected via a pump connector 174 to a gas pump (not shown) for drawing gas through the dual-transducer temperature sensor 114A. Preferably the dual-transducer temperature sensor is constructed as a module 176 that permits connecting to upstream channel 177 of the gas stream A and pump connector 174, as well as connecting to electrical leads. An electrical connector 178, having leads 180A, 180B, 180C, 180D for connecting with the metal layers 134, 132, 148, 146, respectively, can be used to provide electrical communication to the dry-transducer reference thermocouple 130 and wet-transducer thermocouple 144. It is contemplated that module 176, as well as the structures connected thereto, including the gas channel upstream, the pump connector 174, and the electrical connector 178 are constructed to allow the various pieces to fit together by "snap-on" fittings so that no elaborate securing mechanisms such as screw, clamps, rivets, adhesive, and the like are needed. FIG. 8C shows a sectional view perpendicular to those of FIG. 8A and FIG. 8B.

FIG. 9A shows another embodiment of a vapor sensor in which micropores are present in a tubular thermocouple junction. In this case, the thermocouple junction, at which two metals meet, wraps around to result in a shape of the surface of a cylinder, i.e., a tubular thermocouple junction. FIG. 9B shows a portion of the tubular thermocouple junction with the adjacent layers in cross-section. In FIGS. 9A and 9B, the thermocouple junction 182 is tubular and is made of a first metal layer 184A and a second metal layer 184B. The two tubular layers 184A and 184B extend from two different ends towards each other and contact and overlap at a portion 184C. The lumen 185 of the tubular thermocouple junction 182 is filled with the liquid whose vapor is being detected. An insulator layer 187 is shown, insulating the metal layers 184A and 184B from the liquid in the lumen 185. Micropores (or perforations) 186 traversing from the liquid through the insulator layer 187 and the metal layers 184A, 184B are present at the thermocouple junction 182 to allow the liquid to pass from the lumen 185 through the tubular thermocouple junction 182 to the outside surface for evaporation. The gas stream, represented by the arrows D flows pass the thermocouple junction 182 and vaporized the liquid from the micropores 186 in the thermocouple junction 182. The evaporative cooling at the vicinity of the micropores is measured via leads connected to the two ends of the tube and to a thermocouple output meter. Practically, the metal layers of the thermocouple junction 182 can be formed by deposition on an insulator tube. However, the insulator tube is not necessary for the thermocouple junction to work and thus the thermocouple junction can be formed by other means, such as forming a metallic tube on a tube of another metal for thermocouple junction.

Making the vapor sensors

The vapor sensors of the present invention are well suited for fabrication by automated processes. In some preferred embodiments, since the dual-transducer temperature sensors of the present invention are primarily made of layered materials, they are particularly adaptable for manufacturing processes well known in integrated circuit fabrication. For example, the substrate 138 can be silicon, silicon dioxide, polysilicon, silicon nitride, and the like; the thermal insulator 137 can be silicon nitride, polyimide, or other suitable polymers of low thermal conductivity; the metal layers for thermocouples can be any bimetallic layer combinations suitable for thermocouple constructions.

As stated previously, methods for fabricating semiconductors can be employed for construction of the layered structures for forming the substrate, thermal insulator, the thermocouples, and the like of the present invention. As an illustration, an embodiment of the dual-transducer temperature sensor can be made with a silicon substrate, a $SiO_2$ sacrificial layer for etching depressions and cavities in the silicon, a polyimide layer for the thermal insulator, copper versus constantan for the thermocouple bimetallic layers.

Bimetal layer combination for thermocouples are known in the art, such as platinum versus rhodium, copper versus constantan, iron versus constantan, nickel-chromium alloy versus nickel-aluminum alloy, and the like. For a list of materials suitable of thermocouple construction, see Manual on the use of Thermocouples in Temperature Measurement, ASTM manual STP 470B, 1981. Other materials suitable for thermocouples are reported by Julian Gardner, *Microsensor, Principles and Applications,* ch. 5, John Wiley and Sons, 1994. Methods for laying metallic layers and etching them to achieve the desired dimensions are known in the art.

As is known in the art, glass and $SiO_2$ can be etched with suitable chemicals, e.g., buffered hydrofluoric acid (HF) mixtures; silicon can be etched with potassium hydroxide (KOH), preferably with tetramethyl ammonium hydroxide (TMAH); glass, $SiO_2$, polysilicon, and silicon nitride can be dry-etched with plasma chemistry known to one skilled in the art; and silicon nitride can also be wet-etched with phosphoric acid ($H_3PO_4$). It is also known that these etching methods affect each material (e.g., silicon, silicon nitride, polysilicon, $SiO_2$, NiFe) differently. This difference is due to the materials' inherent physical and chemical properties. The different etch rates for such materials using a wide variety of etchants will allow the ability to etch differentially one material quickly and another very slowly. Such differences in etching rate can be advantageously used for making cavities, reservoirs, and the like.

Etching methods for forming structures (including microstructures) and etching materials used in solid-state semiconductor technology are known in the art. Examples of methods for forming microstructures include, e.g., Judy and Muller, "Magnetic Microactuation of Torsional Polysilicon structures," *Dig. Int. Conf. Solid-State Sensors and Actuators,* Stockholm, Sweden, Jun. 25–29, 1995, pp. 332–339; and Pister et al. "Microfabricated Hinges," *Sensors and Actuators,* A. 33, 1992, pp. 249–256, of which the description on methods of making microstructures are incorporated by reference herein.

Methods for etching silicon dioxide are described in Steinbruchel et al., "Mechanism of dry etching of silicon dioxide—A case study of direct reactive ion etching," *J. Electrochem. Soc. Solid-state and Technology,* 132(1), pp. 180–186, Jan. 1985; and Tenney et al., "Etch Rates of Doped Oxide in Solutions of Buffered HF," *J. Electrochem. Soc. Solid State and Technology,* 120 (8), pp. 1091–1095, Aug. 1973. Polysilicon etching is described by Bergeron et al., "Controlled Anisotropic Etching of Polysilicon," *Solid State*

*Technologies,* August 1982, pp. 98–103; and B. L. Sopori, "A New Defect Etch for Polycrystalline Silicon," *J. Electrochem. Soc. Solid State and Technology,* 131 (3), pp. 667–672, Mar. 1984. Silicon nitride etching is described by van Gelder et al., "The etching of Silicon Nitride in Phosphoric Acid with Silicon Dioxide as a mask", *J. Electrochem. Soc. Solid State and Technology,* 114 (8), Aug. 1967, pp. 869–872. Silicon etching is described by M. J. Declercq, "A New CMOS Technology Using Anisotropic Etching of Silicon," *IEEE J. of Solid State Circuits,* Vol. SC-10, No. 4, Aug. 1975, pp. 191–196; K. E. Bean, "Anisotropic Etching of Silicon," *IEEE Trans. Electron. Devices,* Vol. ED-25, No. 10, Oct. 1978, pp. 1185–1193; Osamu Tabata, "pH-controlled TMAH etchants for silicon micromachining," *Sensors and Actuators,* A53, 1996, pp. 335–339, and Robbins, et al., "Chemical Etching of Silicon II. The system of HF, $HNO_3$, $H_2O$, and $HC_2H_3OO_2$," *J. Of The Electrochemical Society,* 107 (2), Feb. 1960, pp. 108–111. These etching methods are incorporated by reference herein.

An example of the thermal insulator is polyimide, e.g., PI-2611 from DuPont Company (Wilmington, Del.). A polyimide layer is typically formed by spinning. Such a layer can be etched by dry plasma etching. Polyimide materials suitable for such applications are available commercially from chemical suppliers such as DuPont Company and Ciba Geigy Corp. (Greensboro, N.C.). Methods of spinning and etching a polyimide layer are known in the art. See, e.g., Ahn, et al., "A Planar Variable Reluctance Magnetic Micromotor with Fully Integrated Stator And Wrapped Coils," *Proc. IEEE Micro Electro Mechanical Systems (MEMS '93),* Fort Lauderdale, Fla., Feb. 7–10, 1993. Other polymeric material, such as polyolefin, acrylic material, styrene-based polymers, etc., known to one skilled in the art can be used.

As previously described, other electrical temperature sensing devices and materials, such as thermistors, can be used in place of thermocouples for sensing temperature differences and providing electrical signals for calculating vapor concentration or determining the presence or absence of a vapor in the gas stream. Suitable thermistors include miniature beads or strips of sintered oxides such as barium oxide or strontium oxide and their mixtures in various proportions. These beads or strips are typically coated with a thin layer of glass to protect them from the ambient. The beads and strips are typically connected with platinum/indium leads which are connected in a circuit to measure the electrical resistance of the bead or strip. The strips or beads can be formed by pressing together the appropriate sintered oxides and then encapsulating them in a glass layer. The strips of thermistors can be made so that they have micropores passing through them, each micropore to an opening for liquid vaporization. Thermistors and methods of making them are known in the art.

A device with tubular heat sensors, e.g., one that is shown in FIG. 9A, can be made, for example, by first forming a support tube and then depositing the thermocouple junction on the tube and subsequently forming the micropores on the tube as well as the thermocouple junction. The thermocouple junction can be formed by coating with the two metals sequentially. One can also coat the support tube with a thermistor material for forming a thermistor for temperature measurements during evaporative heat loss. Micropores can be formed on the tube with perforating tools and techniques such as drilling, etching, and laser ablation. The micropores can also be formed by masking before the metal layers are deposited.

Using the vapor sensor

A vapor sensor of the present invention can be used in a gas stream to measure the vapor concentration of a liquid or the presence of the vapor in the gas stream relatively independent of the velocity of the gas stream. Although water-humidity examples are described in more detail in this disclosure, it is to be understood that a vapor sensor according to the present invention can be made to sense the concentration of the vapor of other liquids, such as organic liquids including alcohols, e.g., ethanol, methanol, propanol, isopropanol, butanol; ketone, e.g., acetone; aldehyde, e.g., formaldehyde; aromatic liquid, e.g., benzene and toluene; chlorinated organic such as carbon tetrachloride, and the like. For convenience of description, as used herein, the term "humidity" refers to the degree of saturation of a vapor of a liquid in a gas, wherein the vapor may be water vapor or a vapor of other liquids and the gas may be air or other gases. In a more specific sense, as in equations herein, humidity refers to the concentration of the vapor in the gas expressed as mass of the vapor in unit mass of a vapor-free gas.

To use a vapor sensor of the present invention, a look up table, graph, or computer database can be obtained by calibrating a vapor sensor with a specific kind of dual-transducer temperature sensor with conditions corresponding to various concentrations and temperatures in a specific gas. For example, a psychrometric chart or graph for water vapor in air can be obtained by calibrating a humidity sensor with different samples of air having a variety of water vapor concentration in air at different temperature. Furthermore, such data can be stored electronically in a digital computer such that the electrical signals generated by the reference temperature sensors and the wet-transducer temperature sensors can be correlated with the vapor concentration in the gas sample and temperature. The computer can be programmed to indicate the corresponding vapor concentration depending on the electrical signals of the reference and wet-transducer temperature sensors. As used herein, the terms "psychrometry" and "psychrometric" refers to the determination of the concentration of a vapor of a vaporizable (i.e., volatile) liquid in a gas. Examples of vaporizable (volatile) liquids are those that have a vapor pressure at room temperature of 0.1 mmHg or above. A person skilled in the art will understand that, knowing the electrical property of the temperature sensors, the electrical signals therefrom can be used for calculating the vapor concentration without literally calculating the temperatures numerically.

The theory of psychrometry is known in the art. For example, publications such as McCabe and Smith, *Unit Operations of Chemical Engineering,* McGraw-Hill, Ch. 24, 3rd ed, (1956) and Robert Perry (ed.), *Chemical Engineers' Handbook,* Chapters on "Psychrometry" and "Solids drying fundamentals," McGraw-Hill (1963) describe humidification operations, psychrometric charts, and the theory of wet-bulb temperature versus dry-bulb temperature. Briefly, the dry-transducer temperature, corresponding to the dry-bulb temperature of McCabe or Perry, as measured by the reference temperature sensor in the present invention, represents the temperature of the gas in which the vapor content is to be determined. The wet-transducer temperature, corresponding to the wet-bulb temperature of McCabe or Perry, is the steady state, non-equilibrium temperature reached by a small mass of liquid under adiabatic conditions in a continuous stream of gas. In the present invention, as long as the liquid does not move past the wet-transducer temperature sensor in an excessive rate, the conditions approximates an adiabatic condition to the vapor sensor to be functional.

When the dual-transducer temperature sensor is placed in a gas stream, initially the temperature of the wet-transducer temperature sensor is about equal to or would tend to approach that of the gas, much as what the reference temperature sensor would do. If the gas is not saturated with the vapor of the liquid in question, liquid would evaporate from the liquid surrounding the wet-transducer temperature sensor. Because the condition is adiabatic, the latent heat of vaporization is supplied from the wet-transducer temperature sensor and the surrounding air. As the temperature of the wet-transducer temperature sensor falls below that of the gas, sensible heat is transferred from the gas to the wet-transducer temperature sensor and the liquid at the micropore opening. Eventually a steady state is reached, at which point the heat supplied by the gas to the wet-transducer temperature sensor and to the liquid is equal to the heat loss by evaporation of the liquid in the vicinity of the wet-transducer temperature sensor. At this point the wet-transducer temperature sensor settles at a temperature, the wet-transducer temperature. For the steady state to occur in a condition better suited for measuring vapor concentration, it is preferred that the velocity of the gas passing over the wet-transducer temperature sensor be adequately high so that radiation heat transfer is small compared to conduction and convention heat transfer between the gas and the liquid, and that the surface area from which water can evaporate stays constant.

Now, the energy transfer of psychrometry will be described. It is noted although water evaporation is used as an illustrative example, and the term "humidity" is used, the mathematics is equally applicable to other liquids, as is evident to one skilled in the art. The heat transfer can be represented by the following equation:

$$q=MN\{L_w+C(t-t_w)\} \tag{1}$$

where q is the rate of sensible heat transferred to the liquid, M is the molecular weight of the vapor evaporated from the liquid, N is the molar rate of transfer of vapor, $L_w$ is the latent heat of vaporization of the liquid, C is the heat capacity of the vapor, t is the temperature of the gas, and $t_w$ is the wet-transducer temperature. Because the value of the term "$C(t-t_w)$" is usually very small compared to $L_w$ in Eq. (1), the relationship between humidity and the wet and dry-transducer temperature can be shown by the following equation:

$$(H-H_w)L_w=-K(t-t_w) \tag{2}$$

where H is the humidity in question, $H_w$ is the saturation humidity at the wet-transducer temperature $t_w$, $L_w$ is the latent heat of evaporation of the vaporization of the liquid at temperature $t_w$, and K is a constant that depends on the molecular weight of the dry gas, the heat transfer coefficient, and the mass transfer coefficient between the liquid and the gas.

Data for different conditions on the parameters in Eq. (2) can be obtained by routine experimentation by one skilled in the art. Such data for some common liquid and vapor mixtures are available in the literature. For example, psychrometric data in graphical form are available for air-water mixture, air-benzene, air-toluene, air-carbon tetrachloride in Perry, supra. Based on such data, after obtaining the reference temperature and wet-transducer temperature, one can determine the humidity (i.e., vapor concentration in the gas) by looking up the data. Knowing the temperature of, the gas stream, relative humidity (in %) and absolute humidity (in mass of vapor per unit mass of gas) can be converted to each other.

Furthermore, Eq. (2) can be programmed in a computer, e.g., an electronic digital computer, microprocessor, and the like, for indicating the humidity (i.e., vapor concentration) based on the reference temperature (i.e., dry-transducer temperature) and the wet-transducer temperature. For determining the concentration of a vapor other than water in a gas, the material, e.g., bimetallic thermocouple material, thermal insulator, and the like, which may contact the liquid should be selected to be compatible with the liquid and vapor, as well as the gas in which the dual-transducer temperature sensor is to be used. Further, the algorithm for the calculation of temperature, vapor concentration, the control of equipment, or direct conversion from electrical signals from the temperature sensors to vapor concentration, etc., can be stored in a computer, chips, storage devices (such as floppy disks, hard disks, compact disks, tapes), and the like for long or short term storage.

The vapor sensor of the present invention can be adapted in an embodiment to be used as a conventional humidity sensor for measuring water humidity in atmospheric air, much like the conventional dry and wet bulb humidity sensor, with the exception that instead of a wick, micropores in close proximity to temperature transducers are used. Other embodiments can be adapted to measure the concentration of, e.g., organic vapors in gas streams. In these cases, any organic materials used, e.g., thermal insulators, are selected to be compatible with the gas and vapor and such that the heat and mass transfer are adequate for the vapor sensor (which in these cases measure temperature relating to the non-aqueous vapor concentration) to function properly. For liquids that vaporize faster than water at a particular temperature, e.g., room temperature of about 25° C., adequate micropores in the apparatus should be provided to transfer liquid at an adequate rate so as not to mass-transfer-limit the apparatus.

Such vapor sensors can be used in a wide variety of applications. For example, they can be used in traditional humidity measurement for weather reporting, for monitoring gas in a chemical plant, for measuring gases in a patients breath, as well as for detection of vapor for monitoring a drying process.

Although the preferred embodiment of the present invention has been described and illustrated in detail, it is to be understood that a person skilled in the art, based on the present disclosure, can make modifications within the scope of the invention.

What is claimed is:

1. A sensor for sensing in a gas stream a vapor of a liquid, comprising:

a micropore having an evaporation end and having a lumen to conduct liquid from a supply of the liquid for evaporation at the evaporation end; and a wet temperate sensor having a heat sensitive part in contact with the liquid in the micropore, the heat sensitive part circumscribing the micropore and forming part of the lumen, wherein heat loss due to evaporation of the liquid when the wet temperature sensor wet with the liquid is placed in the gas stream will result in the temperature sensed by the wet temperature sensor being lower than the non-evaporative temperature of the gas stream sensed by at least one reference temperature sensor, the lowering in temperature being measurable to determine the concentration of the vapor in the gas stream.

2. The sensor according to claim 1 comprising a plurality of the micropores neighboring one another and supplied by a common liquid reservoir to increase heat transfer to the wet temperature sensor.

3. The sensor according to claim 1 wherein the heat sensitive part has the form of a layer having two sides wherein the micropore passes through the heat sensitive part from one side to the other side.

4. The sensor according to claim 3 wherein the layer-form heat sensitive part is supported by a heat insulator layer which thermally insulates the heat sensitive part from the reservoir, the micropore traversing through the heat insulator to have liquid communication with the liquid reservoir.

5. The sensor according to claim 4 wherein the heat sensitive part is one of a thermocouple junction and a thermistor.

6. The sensor according to claim 3 wherein the heat sensitive part comprises a surface junction formed between a layer of a first material and a layer of a second material, said surface junction having electrical property that changes according to temperature, and wherein the micropore traverses through said layers of first material and second material.

7. The sensor according to claim 4 further comprising a substrate defining the liquid reservoir, a heat insulator layer interposing between the heat sensitive part and the substrate, and further comprising additional plurality of micropores traversing through the heat sensitive part to the liquid reservoir to increase evaporation for achieving steady state temperature at the wet temperature sensor.

8. The sensor according to claim 4 further comprising a plurality of wet temperature sensors and sets of micropores, each set being sensed by a different wet temperature sensor and in liquid communication with a reservoir of a different liquid, such that the temperature of liquid evaporating in each set can be compared to the temperature sensed by at least one reference temperature sensor to determine the vapor concentration of each of said liquids.

9. The sensor according to claim 8 wherein each set of micropores comprises a plurality micropores supplied with the same liquid.

10. The sensor according to claim 7 further comprising a gas including gap interposing between the heat insulator layer and at least a portion of heat sensitive part to reduce conductive heat transfer through solid to the heat sensitive part.

11. The sensor according to claim 6, wherein the reference temperature sensor comprises a heat sensitive part including a surface junction of a layer of a third material and a layer of a fourth material wherein the electrical property of the surface junction changes according to a change in the non-evaporative temperature of the gas stream.

12. The sensor according to claim 11 wherein the second material is the same as the fourth material, the layer of second material in the wet temperature sensor being electrically connected to the layer of fourth material in the reference temperature sensor such that the difference in electrical signal between the layer of the first material in the wet temperature sensor and the layer of the third material in the reference temperature sensor is indicative of the temperature difference between the wet temperature and the reference temperature.

* * * * *